United States Patent
Maurer et al.

(10) Patent No.: US 6,803,038 B1
(45) Date of Patent: Oct. 12, 2004

(54) USE OF BROMELAINE PROTEASES FOR INHIBITING BLOOD COAGULATION

(75) Inventors: Rainer Maurer, Berlin (DE); Klaus Eckert, Berlin (DE); Edyta Grabowska, Berlin (DE); Klaus Eschmann, Kleinblittersdorf (DE)

(73) Assignee: Ursapharm Arzneimittel GmbH (DE)

( * ) Notice: Subject to any disclaimer, the term of this patent is extended or adjusted under 35 U.S.C. 154(b) by 0 days.

(21) Appl. No.: 09/674,738
(22) PCT Filed: Jul. 15, 1998
(86) PCT No.: PCT/EP98/04406
§ 371 (c)(1),
(2), (4) Date: Jul. 25, 2001
(87) PCT Pub. No.: WO00/03729
PCT Pub. Date: Jan. 27, 2000

(51) Int. Cl.$^7$ .............................................. A61K 38/46
(52) U.S. Cl. .................................................. 424/94.65
(58) Field of Search ........................ 424/94.65; 435/23, 435/219

(56) References Cited

U.S. PATENT DOCUMENTS

| | | | |
|---|---|---|---|
| 5,767,066 A | * 6/1998 | Barnwell | 514/2 |
| 5,824,305 A | * 10/1998 | Mynott et al. | 424/94.65 |
| 5,928,640 A | * 7/1999 | Mynott | 424/94.63 |
| 6,335,427 B1 | * 1/2002 | Mynott et al. | 530/379 |

FOREIGN PATENT DOCUMENTS

| | | |
|---|---|---|
| DE | 63295515 | 12/1988 |
| DE | 4130221 | 3/1993 |
| DE | 4302060 | 7/1994 |
| WO | WO 95/00169 | 1/1995 |
| WO | WO 98/38291 | 9/1998 |

OTHER PUBLICATIONS

Munzig E et al., Bromelain protease F9 reduces the CD44 mediated adhesion of human peripherial blood lymphocytes to human umbilical vein endothelial cells, FEBS Letters, 1994, 351, 215–218.*
Ritonja A. et al. Stem bromelain: amino acid sequence and implication for weak binding of cystatin, FEBS Letters, 1989, 247, 419–424.*
Harrach T. et al. Isolation and characterization of two forms of an acidic bromelain stem proteinase, Journal of Protein Chemistry, 1998, 17, 351–361.*
Sunny et al., "Effect of Fabrication, Sterilization and Mediators—Blood Compatibility of Polyurethanes", J. of Biomaterials Applications, vol. 6, Jan. 1992, pp. 261–273.
Harrach et al., "Isolation and Partial Characterization of Basic Proteinaases from Stem Bromelaine", J. of Protein Chemistry, vol. 14, No. 1, 1995, pp. 41–52.
Taussig et al., "Bromelaine, the Enzyme Complex of Pineapple and its Clinical Application, an Update", J. of Ethnopharmacology, vol. 22, pp. 191–203.
Murachi et al., *Fractionation and Specificity Studies on Stem Bromelain*, The Journal of Biological Chemistry, vol. 235, No. 1, Jan. 1960, pp. 99–107.

* cited by examiner

*Primary Examiner*—Rebecca E. Prouty
*Assistant Examiner*—Malgorzata A. Walicka
(74) *Attorney, Agent, or Firm*—Bell, Boyd & Lloyd LLC

(57) ABSTRACT

The present invention relates to the use of bromelaine proteases for inhibiting blood coagulation, especially for stimulating the production of plasmin, for inhibiting the production of fibrin and for inhibiting the adhesion of human thrombocytes on endothelilum cells. Especially the basic proteases isolable from raw bromelaine have proved to be particularly suitable proteases.

1 Claim, No Drawings

SEQUENCE LISTING

```
<160> NUMBER OF SEQ ID NOS: 2

<210> SEQ ID NO 1
<211> LENGTH: 20
<212> TYPE: PRT
<213> ORGANISM: pine-apple (Bromeliacea)

<400> SEQUENCE: 1

Val Pro Gln Ser Ile Asp Trp Arg Asp Tyr Gly Ala Val Thr Ser Val
 1               5                  10                  15

Lys Asn Gln Asn
            20

<210> SEQ ID NO 2
<211> LENGTH: 20
<212> TYPE: PRT
<213> ORGANISM: pine-apple (Bromeliacea)

<400> SEQUENCE: 2

Val Pro Gln Ser Ile Asp Trp Arg Asp Ser Gly Ala Val Thr Ser Val
 1               5                  10                  15

Lys Asn Gln Gly
            20
```

USE OF BROMELAINE PROTEASES FOR INHIBITING BLOOD COAGULATION

The present invention relates to the use of bromelaine proteases, preferably basic bromelaine proteases, notably for inhibiting the blood coagulation system, especially for stimulating the production of plasmin, for inhibiting the production of fibrin and for inhibiting the adhesion of human thrombocytes to endothelium cells.

Bromelaine is a mixture of quite different proteins that may be isolated from plants of the family Bromeliaceae, the exact composition of which could so far not yet be completely characterized due to the complexity and variety of the components contained therein. It could, however, be shown that bromelaine contains different phosphatases, cellulases, glycosidases, cysteine proteases and the peptide inhibitors thereof, as well as additional not yet more closely identified components. The material and quantitative composition of bromelaine, however, varies in response to the origin and the isolation procedure from the respective source, so that different methods for isolating the raw product, for standardizing the same as well as for purifying specific components contained therein, have been developed. As used herein, the term "bromelaine" or other like terms is meant to be interchangeable with term "bromelain."

Some of the components in bromelaine have already been identified more closely. Thus, it is reported by Murachi et al. in The Journal of Biological Chemistry 1 (1960), 99–107, that bromelaine contains at least 5 similarly acting proteases with a different substrate specificity and a different pH optimum.

During studies performed with bromelaine it has, moreover, been found that said mixture can also be used as a medicament for treating different states of diseases.

Thus, DE 41 30 221 proposes the use of papain and/or trypsin, specific proteolytic enzymes derived from the bromelaine mixture, for the production of a medicament, which is to be suitable for treating autoimmune diseases. According to said patent, the papain, or the trypsin respectively acts on proteins participating in the development of autoimmune diseases, which comprise a $C_H2$-domain.

The use of bromelaine as a mixture for cancer therapy and/or metastasis prophylaxis is moreover disclosed in DE 43 02 060, in which it is assumed that bromelaine acts on CD44, a strongly glycosylized surface protein present in different cells of the organism, which is said to play a role in the development of tumors.

The isolation and characterization of a protease from the bromelaine mixture is explained in WO 95/00169, which acts on the synthetic pathway of cyclic nucleotides. The enzyme designated as "Stem Bromelaine Protease" comprises 213 amino acids and is to obviate diseases, such as the formation of tumors, atherosclerosis or bacterial infections.

Due to the development in the field of purification techniques it has been possible to isolate and partially also characterize additional components from the bromelaine mixture. Thus, it was disclosed by Harrach et al. in The Journal of Protein Chemistry 14 (1995), 41–52, that bromelaine contains at least 8 basic proteases, which could be fractioned by means of FPLC-cation exchange-chromatography. Also, the existence of two forms of acidic proteases could be shown (Maurer et al., Journal of Protein Chemistry 17 (1998), 351–361).

Although different medical fields of application for bromelaine have been found, there is a need to find additional applications for bromelaine. It would thereby be desirable, due to the not yet completely understood interactions of the individual components in the mixture, not to use the mixture itself in the respective field of application, but only the component of the mixture responsible for the respective purpose. A problem arises in this respect, however, as it cannot be predicted whether individual components are effective by themselves in an isolated state without other additional substances present in the bromelaine mixture, or whether they rather require additional components present in the bromelaine mixture as auxiliary substances, which have so far not yet been identified.

It is an object of the invention to provide additional possibilities to use bromelaine, especially the components thereof.

Another object of the invention resides in identifying the component(s) responsible for the respective medical use, and in providing access thereof to a medical use.

The inventors have carried out extensive studies and have surprisingly found, that an inhibition of blood coagulation can be achieved solely with the proteases present in the bromelaine mixture, without the other components present in said mixture.

Consequently, the above-mentioned problem is solved by using the proteases present in the bromelaine mixture for inhibiting blood coagulation.

It has been shown that especially the production of plasmin is stimulated by the bromelaine proteases, while the formation of fibrin and the adhesion of thrombocytes on endothelium cells—all of which are processes playing a significant role in blood coagulation—are inhibited.

In a preferred embodiment of the invention especially basic proteases are applied for the indicated purpose, preferably the bromelaine proteases obtained as fractions F4, F5 or, more preferably, F9 in accordance with the method described by Harrach et al. in the Journal of Protein Chemistry 14 (1995), 41–52.

The protease contained in fraction F4 has a molecular weight of about 24.4 KDa and an optimal activity at a pH in the range of about 4 to 5.5. The protease further comprises the following amino acid sequence:

Val Pro Gln Ser Ile Asp Trp Arg Asp Tyr

Gly Ala Val Thr Ser Val Lys Asn Gln Asn

The protease contained in fraction F5 has a molecular weight of about 24.5 KDa and an optimal activity at a pH in the range of about 3.5 to 5. The protease further comprises the following amino acid sequence:

Val Pro Gln Ser Ile Asp Trp Arg Asp Tyr

Gly Ala Val Thr Ser Val Lys Asn Gln Asn

The protease contained in fraction F9 has a molecular weight of about 23.4 KDa and an optimal activity at a pH in the range of about 6 to 8. The protease further comprises the following amino acid sequence:

Val Pro Gln Ser Ile Asp Trp Arg Asp Ser

Gly Ala Val Thr Ser Val Lys Asn Gln Gly

It has surprisingly shown that an effective inhibition of blood coagulation can be achieved by using bromelaine proteases, and that said inhibition can be obtained merely with the proteases isolated from said bromelaine mixture, without other additional components present in the bromelaine mixture playing a role.

The proteases can be administered to a subject in a manner already known in connection with the bromelaine mixture, i.e. by intravenous or intraperitoneal or preferably by oral administration, wherein the active substances are then formulated with excipients commonly used in the prior art, for passing the proteases through the gastrointestinal tract in an active form so as to guarantee a systemic availability.

The proteases can be isolated in accordance with conventional methods. Especially a purification as indicated by Harrach et al. in the Journal of Protein Chemistry 14 (1995), 41–52 and by Maurer et al. in the Journal of Protein Chemistry 17 (1998), can be applied. Upon purification, said proteases can be initially sequenced, and the corresponding gene can be isolated from the genome of e.g. the pineapple by means of molecular-biological methods. By means of molecular-biological methods a recombinant protein can then be provided in a conventional manner.

The invention will now be explained in more detail by means of the following examples, which merely are explanatory and are not to be construed to limit the present invention.

The proteases used in the present invention, especially the basic proteases, are isolated according to Harrach et al., The Journal of Protein Chemistry 14 (1995), 41–52 and according to Maurer et al., The Journal of Protein Chemistry 17 (1998). The contents of said publications are herewith entirely included in the contents of disclosure of the present application.

As disclosed in Harrach (1995), crude bromelain extracts from pineapple stems (*Ananas comosus*) were fractionated by two-step FPLC-cation-exchange chromatography. At least eight basic proteolytically active components were detected. The two main components F4 and F5 together with the most active proteinase fraction F9 were characterized by SDS-PAGE, mass spectroscopy, multizonal cathodal electrophoresis, partial amino acid sequence, and monosaccharide composition analysis. F9 amounts included about 2% of the total protein and had a 15 times higher specific activity against the substrate L-pyroglutamyl-l-phenylanalyl-l-leucine-p-nitroanilide (PFLNA) than the main component F4. The molecular masses of F4, F5, and F9 included 24,397, 24,472, and 23,427, respectively, as determined by mass spectroscopy. Partial N-terminal amino acid sequence analysis (20 amino acids) revealed that F9 differs from the determined sequence of F4 and F5 by an exchange at position 10 (tyrosine serine) and position 20 (asparagine glycine). F4 and F5 contained fucose, N-acetylglucosamine, xylose, and mannose in ratio of 1.0:2.0:1.0:2.0, wherein 50% of the proteins appeared to be glycosylated, F9 was found to be unglycosylated. Polyclonal antibodies (IgG) against F9 detected F4 and F5 with tenfold reduced reactivity. The pH optimum of F4 and F5 was between pH 4.0 and 4.5. For F9, the pH optimum was close to neutral pH. The kinetic parameters for PFLNA hydrolysis were similar for F4 ($K_m$ 2.30 mM, $k_{cat}$ 0.87 $sect^{-1}$) and F5 ($K_m$ 2.42 mM, $k_{cat}$ 0.68 $sec^{-1}$), and differed from F9 ($k_m$ 0.40 mM, $k_{cat}$ 3.94 $sec^{-1}$).

As disclosed in Maurer (1998), two forms of an acidic bromelain proteinase isolated from crude bromelain, an extract from pineapple stem, were found by a two-step FPLC purification procedure. The basic main components were removed by cation exchange chromatography and the breakthrough fraction was further resolved by anion exchange chromatography into 15 protein fractions, only two of which, called SBA/a and SBA/b, were proteolytically active. These components were characterized by electrospray mass spectroscopy (ESMS), isoelectric focusing, N-terminal amino acid sequence analysis, monosaccharide analysis, and enzymatic parameters. The molecular masses of SBA/a and SBA/b were determined by ESMS to be 23,550 and 23,560, respectively. The isoelectric points (pI) of the two bands of SBA/a were 4.8 and 4.9. SBA/b focused as a single band at pI=4.8. Partial N-terminal amino acid sequences (II residues) were identical to SBA/a and SBA/b and identical with those of stern bromelain (e.g., the basic main proteinase of the pineapple stem) and fruit bromelain (e.g., the acidic main proteinase of the pineapple fruit). Both components are highly glycosylated. Hydrolysis of SBA/a yielded about twofold more monosaccharide per protein than SBA/b. The comparison of the catalytic properties of SBA/a with those of SBA/b revealed no relevant differences in the hydrolysis of three peptidyl-NH-Mec substrates and in the inhibition profiles using chicken cystatin and E-64, thus indicating that these components can be considered as two forms of a single enzyme. Both forms are not inhibited very much by chicken cystatin and are slowly inactivated by E-64 and thus are nontypical cysteine proteinases of the papain superfamily.

As example of the effects of bromelaine proteases on blood coagulation, the fraction F9 isolated according to the above-mentioned documents will be used substitutionally.

Effects of Bromelaine F9 on the Fibrinolysis

For determining the effect, a method based on the use of a chromogenic substrate in a photometric system is applied. By means of the used test kit Berichrom-Pasminogen (Behring) the plasminogen of the sample is transferred into a complex by streptokinase. During the kinetic test, the release of plasmin can be detected in terms of quantity through the extinction increase by adding the plasmin substrate.

EXAMPLE 1

In this experiment, the fibrinolytic activity of bromelaine F9, bromelaine base powder (raw product) and streptokinase is compared.

The starting material for determining the fibrinolytic activity of the protease bromelaine F9 to be tested is the citrate plasma of healthy donors. 9 parts of venous blood are mixed with 1 part of sodium citrate solution (0.11 mol/l) and are subsequently centrifuged for 10 min (1500×g). Streptokinase, urokinase, tPA, plasmin substrate, the test substance bromelaine as the plastic cuvettes are preheated to 37° C. in an incubator. 20 ml of the plasma sample, 500 ml of the streptokinase (ready-to-use test kit solution), urokinase (1U/ml), tPA=Actilyse® ($0.58 \times 10^6$ I.E./ml) or of the bromelaine F9 solution are pipetted into the measuring cuvette. Upon mixing, the solution is incubated for 5 min. at 37° C. The reaction is started by adding 100 ml of plasmin substrate (ready-to-use test kit solution). The extinction at 405 nm is measured in response to the concentration of the sample and time.

TABLE 1

Fibrinolytic activity of streptokinase, bromelaine F9 and bromelaine base powder in the plasminogen test

| Time (s) | Streptokinase (kit) | Bromelain F9 ($\mu$g/ml) | | | Bromelaine Base Powder 50 $\mu$g/ml |
|---|---|---|---|---|---|
| | | 5 | 10 | 30 | |
| 30 | 0.284 | 0.23 | 0.315 | 0.304 | 0.356 |
| 60 | 0.523 | 0.424 | 0.485 | 0.559 | 0.449 |
| 120 | 0.741 | 0.610 | 0.611 | 0.795 | 0.507 |
| 180 | 1.078 | 0.929 | 0.929 | 1.036 | 0.551 |

As can be seen from table 1, bromemlaine F9 shows in the kinetic test an effect comparable to that of the streptokinase. The effect of bromelaine F9 is dependent on time and the concentration, the maximum effect is obtained at 30 mg/ml (1.0 U/mg). Already at a concentration of 5 mg/ml (E=0.929) bromelaine F9 is superior to the effect of the bromelaine base powder (0.4 U/mg) in a concentration of 50 mg/ml (E 0.55).

EXAMPLE 2

The objective of this experiment resides in testing whether and to what extent the combination of bromelaine F9 with streptokinase is superior to the effect of streptokinase alone.

TABLE 2

Fibrinolytic activity of streptokinase alone and in combination with bromelaine F9 in the plasminogen test

| Time (s) | Streptokinase (kit) | Streptokinase + Bromelaine F9 |
|---|---|---|
| 30 | 0.284 | 0.246 |
| 60 | 0.523 | 0.479 |
| 120 | 0.741 | 0.728 |
| 180 | 0.078 | 0.939 |

As can be seen from table 2, the combination of bromelaine F9 (10 mg/ml) with streptokinase in the plasminogen test is not superior to the effect of streptokinase alone.

This can be interpreted in that the effect of bromelaine F9 on the fibrinolysis (formation of plasmin) has a characterization similar to that of streptokinase, however, is 10 times higher (relative to the chemical concentration) than that of bromelaine base powder. The effect of bromelaine F9 is dependent on the concentration and time. The kinetics correspond to those of streptokinase alone in said system.

EXAMPLE 3

In this experiment, the fibrinolytic activities of urokinase, tissue plasminogen activator (tPA) and the combinations thereof are compared to that of bromelaine F9.

TABLE 3

Fibrinolytic activity of urokinase, tPA alone and the combination with bromelaine F9 in the plasminogen test

| Time (s) | Urokinase (1 U/ml) | TPA $0.58 \times 10^6$ I.E./ml | Urokinase + Bromelaine F9 (10 µg/ml) | tPA + Bromelaine F9 (10 µg/ml) |
|---|---|---|---|---|
| 30 | 0.2216 | 0.2315 | 0.2757 | 0.2417 |
| 60 | 0.3517 | 0.3215 | 0.3888 | 0.3124 |
| 120 | 0.5830 | 0.4469 | 0.5244 | 0.4680 |
| 180 | 0.7970 | 0.7899 | 0.6640 | 0.7553 |

As can be seen from the comparison of the values illustrated in table 1 and 3, the streptokinase in this test system effects a stronger plasminogen conversion in contrast to urokinase and tPA. The effect of 30 mg/ml bromelaine F9 (tables 1, 3) corresponds to the effect of streptokinase and is superior to the effect of bromelaine base powder. In a combination of bromelaine F9 with the above-mentioned plasminogen activators, no stronger effects can be shown in contrast to the sole effect of urokinase and tPA, or of streptokinase (table 2).

Effect of Bromelaine F9 on the Production of Fibrin from Human Plasma of Healthy Donors In this connection it is the objective to test whether and to what extent bromelaine F9 influences the thrombin-induced production of fibrin from human plasma.

EXAMPLE 4

The starting material is citrate plasma of healthy donors, which is pre-incubated with bromelaine F9 at 37° C. and is mixed with thrombin afterwards. Per test 0.02 ml protease solution are pipetted to 0.05 ml citrate plasma and are incubated for 1 hour. Next, 0.01 ml thrombin (0.2 U/ml) are added and an incubation of 10 min. in the water bath takes place at 37° C. The production of fibrin is evaluated semi-quantitatively, organoleptically under the invert microscope (twenty-fold enlargement).

It is found thereby, that bromelaine F9 (100 mg/ml) just like streptokinase, completely prevents the thrombin-induced production of fibrin from citrate plasma. On the basis of the applied chemical concentration bromelaine F9 is more effective than bromelaine base powder by the factor 2. In contrast thereto, papain (100 mg/ml, specific activity 7.1 U/mg) has no effect under these conditions.

Effect of Bromelaine F9 on the Adhesion of Human Thrombocytes to BKEz-7 Bovine Endothelium Cells Thrombocytes isolated from human whole blood are marked with the fluorescence dye 2,7-bis-(2-carboxyethyl)-5,6-carboxyfluoresceinacetoxymethylester. Permanent BKEz-7 bovine aorta cells (11th–22nd passage) are pipetted into a 96 microtiter plate with 60,000 cells per recess and are incubated overnight. For the thrombocytes-endothelium cell-adhesion-assay $5 \times 10^7$ thrombocytes after an incubation time of 15 min. at 37° C. are optimal. The removal of the non-bonded thrombocytes is effected by washing the cells with KRB-buffer (Krebs-Ringer-bicarbonate buffer with 5.6 mMol Glucose + 1% BSA) twice.

EXAMPLE 5

It is tested in said experiment as to which effect bromelaine F9 has on already adherent thrombocytes. After performance of the thrombocytes-endothelium cell-adhesion-assay the adherent thrombocytes (stimulated with 0.2 U/ml thrombin) are incubated with bromelaine F9 (0.01 mg/ml) for 10 min. at 37° C. As a control, bromelaine base powder (0.1 mg/ml) is tested as well. The resulting thrombocytes bonds on the endothelium cells are compared with those of the samples not treated with protease. As can be seen from table 4, bromelaine F9 reduces the bonding of thrombocytes by 32% (68% bonding), while bromelaine base powder becomes effective only at a concentration of 0.1 mg/ml, with a reduction of the thrombocytes bonding by 40% (60% bonding).

TABLE 4

Adhesion of thrombocytes on BKEz-7 endothelium cells under the influence of bromelaine F9

| − Thrombin | + Thrombin (0.2 U/ml) | + Bromelaine F9 (0.01 µg/ml) | + Bromelaine Base Powder (0.1 µg/ml) |
|---|---|---|---|
| % Adhesion | | | |
| 61* | 100 | 68* | 60* |

The measured fluorescence intensities of the thrombin-stimulated adhered thrombocytes are standardized to 100%;
*p < 0.001 (t-test); in contrast to the adherent, thrombin-stimulated thrombocytes, said differences are statistically significant.

EXAMPLE 6

Isolated human thrombocytes ($5 \times 10^7$/ml) are incubated with bromelaine F9 and bromelaine base powder in different concentrations for 15 min. at room temperature, the proteases are removed by centrifugation (1000×g) and washing, the thrombocytes are resuspended in 1 ml KRB buffer (see above), incubated with 0.2 U/ml of thrombin and used in the adhesion assay on the BKEz-7 cells. The results are illustrated in table 5.

TABLE 5

Adhesion of thrombocytes on BKEz-7 endothelium cells under the influence of bromelaine F9 and Bromelaine Base Powder

| − Thrombin | + Thrombin (0.2 U/ml) | + Bromelaine F9 (µg/ml) 0.005 | + Bromelaine F9 (µg/ml) 0.01 | + Bromelaine Base Powder (0.1 µg/ml) |
|---|---|---|---|---|
| % Adhesion | | | | |
| 61* | 100 | 86* | 75* | 69* |

*p < 0.001 (t-test); in contrast to the adherent, thrombin-stimulated thrombocytes, said differences are statistically significant.

As can be seen from table 5, bromelaine F9 shows a concentration-dependent inhibition of the adhesion of the thrombocytes on the endothelium cells. A small reduction of adhesion of the thrombocytes is determined for bromelaine base powder in a concentration of 0.1 mg/ml.

What is claimed:

1. A method for inhibiting blood coagulation comprising administering a therapeutically effective amount of a composition including a bromelain protease to a subject in need thereof wherein the bromelain protease includes a basic bromelain protease from *Ananas comosus* that has a molecular weight of about 24.4 KDa, an optimal activity at a pH ranging from about 4 to about 5.5 and comprises SEQ ID NO: 1, and wherein the bromelain protease stimulates plasmin production, inhibits fibrin production, and inhibits adhesion of thrombocytes on endothelium cells.

* * * * *